United States Patent [19]
Apelian et al.

[11] Patent Number: 5,292,880
[45] Date of Patent: Mar. 8, 1994

[54] SYNTHESIS OF CAPROLACTAM USING CATALYSTS

[75] Inventors: Minas R. Apelian, Vincentown; Weldon K. Bell, Pennington, both of N.J.; Anthony S. Fung, Chadds Ford, Pa.; Werner O. Haag, Lawrenceville, N.J.; Chaya Venkat, Princeton, both of N.J.

[73] Assignee: Mobil Oil Corporation, Fairfax, Va.

[21] Appl. No.: 30,512

[22] Filed: Mar. 12, 1993

Related U.S. Application Data

[63] Continuation-in-part of Ser. No. 881,282, May 11, 1992, Pat. No. 5,242,676.

[51] Int. Cl.$^5$ ............................................. C07D 201/04
[52] U.S. Cl. .................................................... 540/536
[58] Field of Search ................................. 540/536, 535

[56] References Cited

U.S. PATENT DOCUMENTS

| | | | |
|---|---|---|---|
| 3,016,375 | 1/1962 | Hopkins et al. | 260/239.3 |
| 3,503,958 | 3/1970 | Landis | 260/239.3 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 4,359,421 | 11/1982 | Bell et al. | 260/239.3 A |
| 4,397,827 | 8/1983 | Chu | 423/326 |
| 4,582,815 | 4/1986 | Bowes | 502/64 |
| 4,697,010 | 9/1987 | McMahon | 540/536 |
| 4,709,024 | 11/1987 | Sato et al. | 540/536 |
| 4,717,770 | 1/1988 | Sato et al. | 540/535 |
| 4,927,924 | 5/1990 | Bell et al. | 540/536 |
| 4,968,793 | 11/1990 | Kitamura et al. | 540/536 |
| 5,242,676 | 9/1993 | Apelian et al. | 423/714 |

*Primary Examiner*—Anthony McFarlane
*Attorney, Agent, or Firm*—Alexander J. McKillop; Dennis P. Santini; Lori F. Cuomo

[57] ABSTRACT

A process for catalytically converting cyclohexanone oxime to epsilon caprolactam. The conversion catalyst is a crystalline aluminosilicate zeolite having a Constraint Index greater than 1 and a reduced surface acidity. The surface acidity is reduced by selective surface dealumination of the crystalline aluminosilicate zeolite by contacting the zeolite with dicarboxylic acid, such as oxalic acid.

21 Claims, No Drawings

SYNTHESIS OF CAPROLACTAM USING CATALYSTS

CROSS-REFERENCE TO RELATED APPLICATIONS

This application is a continuation-in-part of copending application Ser. No. 07/881,282 filed May 11, 1992, now U.S. Pat. No. 5,242,676 incorporated herein in its entirety by reference.

FIELD OF THE INVENTION

This application is directed to a process for the catalyzed conversion of oximes to amides. More particularly, it relates to a gas phase catalyzed conversion of cyclohexanone oxime to epsilon caprolactam over a crystalline aluminosilicate zeolite having a reduced surface acidity.

BACKGROUND OF THE INVENTION

Epsilon caprolactam, usually referred to simply as "caprolactam", is a large volume commodity chemical used as a monomer in the production of the commercially important Nylon-6. Although routes to the precursor cyclohexanone oxime vary, all commercial caprolactam production makes use of a Beckmann rearrangement of the oxime. The commercial reaction is carried out in a batch operation in oleum ($H_2SO_4SO_3$) solution. The recovery step in this technology employs an ammonium hydroxide neutralization of the resulting caprolactam-oleum solution, a process generating two moles of by-product ammonium sulfate per mole of product. The sulfate has some value as a low grade fertilizer, but its recovery and/or disposal can add substantial cost to Nylon-6 production. Attempts have been made to circumvent the use of oleum and carry out the reaction in the gas phase, thereby eliminating the undesirable by-product.

A number of patents and publications have appeared which describe such heterogeneous gas phase conversions. Examples of these include U.S. Pat. No. 3,503,958 to P. S. Landis, which describes and claims such conversion using a zeolite such as hydrogen Y; U.S. Pat. No. 3,016,375 which uses as catalyst polyphosphoric acid; and U.S. Pat. No. 4,359,421 to Bell et al. which uses as catalyst a zeolite having a silica to alumina ratio of at least 12 and a Constraint Index of 1 to 12.

U.S. Pat. No. 4,582,815 to Bowes describes and claims a method for preparing binder-free and silica-bonded extrudates of zeolites, including ZSM-5.

U.S. Pat. No. 4,697,010 to McMahon discloses a process for the catalyzed conversion of cyclohexanone oxime to caprolactam over a catalyst composition comprising the hydrogen form of crystals having the structure of ZSM-5 made in the presence of a boron source.

U.S. Pat. No. 4,709,024 to Sato et al. discloses a process for the production of epsilon caprolactam using a crystalline aluminosilicate catalyst having specific Si/Al atomic ratio and a specific acid amount of external surface.

U.S. Pat. No. 4,927,924 to Bell et al. discloses synthesis of caprolactam using a catalyst subjected to steam treatment to reduce its Alpha Value.

The desired rearrangement of cyclohexanone oxime (I) to caprolactam (II) is believed to occur via a protonated intermediate (not shown), according to Equation A.

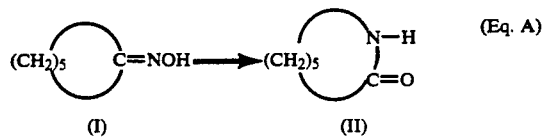

In addition, however, two major side reactions occur, one with the formation of 5-cyanopentene (III) and water (Equation B), and the other forming cyclohexanone oxime (IV) (Equation C).

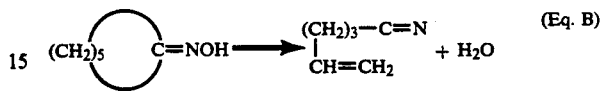

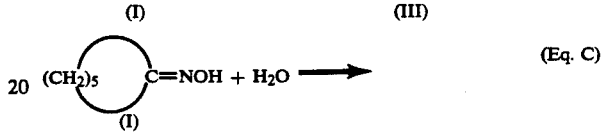

In addition to (III) and (IV) other by-products of unknown structure also are formed.

It is an object of the present invention to provide a heterogenous process which is highly selective for the desired caprolactam product. It is expected that an increase in selectivity of the zeolite catalyst is obtained when cyclohexanone oxime is converted to epsilon caprolactam using a zeolite catalyst having reduced surface acidity to minimize non-selective reactions on the surface acid sites of the zeolite catalysts. It is a further object of the present invention to improve process performance of the zeolite catalyst used in caprolactam synthesis, i.e., better (slower) aging.

SUMMARY OF THE INVENTION

Limiting surface acidity is desirable for preventing undesired reactions on the zeolite surface which are not subject to the shape selective constraints imposed on those reactions occurring within the zeolite interior. However reducing the surface acidity will generally effect a reduction in overall activity of the zeolite. The present invention relates to dicarboxylic acid treatment of zeolites with a C.I. >1 resulting in a reduction in surface acidity without a significant reduction in the desired overall activity based on overall dealumination. The treatment with dicarboxylic acid is believed to selectively remove aluminum from the surface of zeolites having a Constraint Index greater than 1 via a chelating mechanism.

The invention therefore includes in a process for the manufacture of epsilon-caprolactam by contacting cyclohexanone oxime under conversion conditions with a catalyst composition comprising a crystalline aluminosilicate zeolite having a Constraint Index greater than 1 and an Alpha Value in the range of from about 0.1 to 50, the improvement comprising treating said crystalline aluminosilicate zeolite with dicarboxylic acid prior to said contacting step for a sufficient time to effect at least about a 40% reduction in surface acidity with less than about 50% overall dealumination.

DETAILED DESCRIPTION OF THE INVENTION

The conversion reaction of this invention is desirably carried out in a conventional fixed bed reactor, although an ebullated or fluidized bed or other type of reactor can be useful, too, with appropriate changes in the particle size and other physical attributes of the catalyst, such as attrition resistance. The reaction temperature is in the range of about 150° to about 500° C., and more preferably between about 200° and about 400° C. Although the reaction can be carried out at atmospheric pressure, elevated pressure from about 10 psig to about 400 psig, and more preferably from about 50 psig to about 300 psig, is desirable.

It is contemplated that the cyclohexanone oxime feed to the process of this invention may be passed to the reactor neat, i.e., as undiluted solid, melt, or vapor, or it may be diluted with an essentially inert solvent. The use of inert solvent provides a convenient means for storing and transferring the cyclohexanone oxime to the reaction zone. The term "inert solvent" as used herein means a solvent which does not react with the oxime or its reaction product under conversion conditions, and which is not itself converted to a significant extent when contacted with the catalyst under conversion conditions. Useful solvents include the lower boiling saturated hydrocarbons such as hexane and aromatic compounds such as benzene. Regardless whether the cyclohexanone oxime feed is undiluted or dissolved in inert solvent, a carrier gas may be used with the feed to help displace reaction product and any unconverted oxime from the catalyst. Among the gases which may be used are hydrogen, nitrogen, helium, carbon monoxide, carbon dioxide, steam, and the like. Regardless of how the cyclohexanone oxime is introduced, it is contemplated that useful conversion will be obtained at a LHSV (i.e., volumes of cyclohexanone oxime feed per volume of catalyst) within the range of about 0.002 to about 5.0.

Crystalline aluminosilicate zeolites useful in the process of the invention have a Constraint Index greater than 1 and generally have a Constraint Index in the range of greater than 1 to 12.

The method by which Constraint Index is determined is described fully in U.S. Pat. No. 4,016,218, incorporated herein by reference for details of the method. Constraint Index (CI) values for some typical zeolites including some which are suitable in the process of this invention are:

| | CI (at test temperature) |
|---|---|
| ZSM-4 | 0.5 (316° C.) |
| ZSM-5 | 6–8.3 (371° C.-316° C.) |
| ZSM-11 | 5–8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.-399° C.) |

The above-described Constraint Index is an important and even critical definition of those zeolites in which the dicarboxylic acid treatment of the present invention to selectively dealuminate the surface of zeolites is effective. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Accordingly, it will be understood to those skilled in the art that the CI as utilized herein, while affording a highly useful means for characterizing the zeolites of interest, is approximate taking into consideration the manner of its determination including the possibility in some instances of compounding variable extremes. However, in all instances, at a temperature within the above-specified range of 290° C. to about 538° C., the CI will have a value for any given zeolite of interest herein within the approximate range of 1 to 12.

Some zeolite catalysts which are useful in the process of this invention include zeolites ZSM-5, ZSM-11, ZSM-12, and ZSM-48. ZSM-5 is particularly preferred.

ZSM-5 is described in U.S. Pat. No. 3,702,886 and incorporated herein by reference.

ZSM-11 is described in U.S. Pat. No. 3,709,979 and incorporated herein by reference.

ZSM-12 is described in U.S. Pat. No. 3,832,449 and incorporated herein by reference.

ZSM-48 is described in U.S. Pat. No. 4,397,827 and incorporated herein by reference.

Crystal size of the zeolites useful in the process of the present invention is preferably equal to or less than 0.02 microns. However, larger crystals of greater than or equal to 0.1 microns may also be used.

It is well known that crystalline zeolites, including ZSM-5, have a structure consisting of a porous, robust framework. The framework consists principally of silicon tetrahedrally coordinated and interconnected with oxygen bridges. Other framework components of the zeolites useful in the process of this invention may include Group IIIB elements of the Periodic Table, e.g., aluminum, boron, indium and gallium, and iron.

It is important for the purposes of the present invention to control the acid activity of the zeolite catalyst such that the Alpha Value be within the broad range of 0.1 to about 50, and preferably about 0.5 to 40, and most preferably about 1.0 to about 15.

The overall cracking activity is measured by Alpha Value. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395 (1980).

The desired Alpha Value zeolites may be prepared by direct synthesis or converted into the desired Alpha Value form by various conventional techniques, such as steaming, cation exchange, calcination, and acid treatment.

The crystalline aluminosilicate described above may be self-bonded and it also may be incorporated in a matrix, prior to or following the reduction of surface acidity. Such matrix materials include synthetic or natural substances as well as inorganic materials such as clay, silica and/or metal oxides, such as titania or zirconia. The latter may be either naturally occurring or in the form of gelatinous precipitates or gels including mixtures of silica and metal oxides. Naturally occurring clays which can be composited with the zeolite include those of the montmorillonite and kaolin families. These clays can be used in the raw state as originally mined or initially subjected to calcination, acid treatment or chemical modification. These materials, i.e., clays, oxides, etc., function, in part, as binders for the catalyst.

In addition to the foregoing materials, the zeolites may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

The selectivity of such matrix-bonded catalyst is well maintained only if the matrix is substantially non-acidic. Suitability of a matrix material for purposes of this invention can be readily judged by comparing the bonded material with self-bonded zeolite to see if the matrix material has a significantly adverse effect on selectivity. Preparation of self-bound (i.e., without added binder) and of silica-bound ZSM-5 are described in U.S. Pat. No. 4,582,815 to Bowes, incorporated herein by reference. Preferred non-acidic matrix materials are titania, carbon, and silica. Silica is particularly preferred.

Catalysts that have become deactivated during use are readily restored to full activity by periodic regeneration at high temperature, such as 550° to about 700° C., in the presence of oxygen gas. In some instances desorption of adsorbed or occluded matter at about 500° C. in flowing nitrogen gas or hydrogen gas may effect sufficient restoration of activity.

Suitable dicarboxylic acids for use in reducing the surface acidity include oxalic, malonic, succinic, glutaric, adipic, maleic, phthalic, isophthalic, terephthalic, fumaric, tartaric or mixtures thereof. Oxalic acid is preferred. The dicarboxylic acid may be used in solution, such as an aqueous dicarboxylic acid solution.

Generally, the acid solution has a concentration in the range from about 0.01 to about 4M. Preferably, the acid solution concentration is in the range from about 1 to about 3M.

The dicarboxylic acid is generally in a volume solution to volume catalyst ratio of at least about 1:1, preferably at least about 4:1.

Treatment time with the dicarboxylic acid solution is as long as required to provide the desired dealumination. Generally the treatment time is at least about 10 minutes. Preferably, the treatment time is at least about 1 hour.

The treatment temperature is generally in the range from about 32° F. to about reflux. Preferably, the treatment temperature is from about 60° F. to about 200° F., and more preferably from about 120° F. to about 180° F.

More than one dicarboxylic acid treatment step may be employed surface dealumination.

The dicarboxylic acid treatment of this invention may also be combined with other conventional dealumination techniques, such as steaming and chemical treatment.

The dicarboxylic acid selectively dealuminates the surface acid sites of zeolites with a C.I. >1. The presence of surface acid sites, or surface acidity, is determined by the dealkylation of tri-tertbutylbenzene (TTBB), a bulky molecule that can only react with the acid sites on the zeolite crystal surface.

Dealkylation of TTBB is a facile, reproducible method for measuring surface acidity of catalysts. External surface activity can be measured exclusive of internal activity for zeolites with pore diameters up to and including faujasite. As a test reaction dealkylation of TTBB occurs at a constant temperature in the range of from about 25° to about 300° C., and preferably in the range of from about 200° to about 260° C.

The experimental conditions for the test used herein include a temperature of 200° C. and atmospheric pressure. The dealkylation of TTBB is carried out in a glass reactor (18 cm×1 cm OD) containing an 8 gm 14/30 mesh Vycor chip preheater followed by 0.1 gm catalyst powder mixed with Vycor chips. The reactor is heated to 200° C. in 30 cc/gm nitrogen for 30 minutes to remove impurities from the catalyst sample. Ten gm/hr of TTBB dissolved in toluene (7% TTBB) is injected into the reactor. The feed vaporizes as it passes through the preheater and is vapor when passing over the catalyst sample. After equilibrium is reached the nitrogen is switched to 20 cc/min hydrogen. The test is then run for about 30 minutes with the reaction products collected in a cold trap.

The reaction products are analyzed by gas chromatography. The major dealkylation product is di-t-butylbenzene (DTBB). Further dealkylation to t-butylbenzene (TBB) and benzene (B) occurs but to a lesser extent.

Conversion of TTBB is calculated on a molar carbon basis. Dealkylation product weight % are each multiplied by the appropriate carbon number ratio to convert to the equivalent amount of TTBB, i.e., DTBB×18/14, TBB×18/10, and B×18/6. These values are then used in the following conversion equation where asterisks indicate adjustment to the equivalence.

$$\% \text{ Conversion} = \frac{DTBB^* + TBB^* + B^*}{TTBB + DTBB^* + TBB^* + B^*}$$

In addition, thermal background experiments using reactors filled with vycor chips only show no TTBB conversion due to Vycor chips or other reactor components.

The dicarboxylic acid treatment results in less than about 50% overall dealumination, preferably less than about 20% overall dealumination, and more preferably less than about 10% overall dealumination with greater than about 40% reduction in surface acidity, preferably greater than about 50% reduction in surface acidity, and more preferably greater than about 60% reduction in surface acidity.

The following example illustrates the process of the present invention.

EXAMPLE 1

Two ZSM-5 catalysts, one ZSM-5 catalyst treated with oxalic acid and one ZSM-5 catalyst untreated, are tested in a down flow tubular reactor where bed length/diameter varies from about 8 to 12. A 5 wt. % solution of hexanone oxime in benzene is charged to the reactor along with a carrier of nitrogen gas with the reaction in the middle of a three zone furnace at 300° C. and the reactor exit at atmospheric pressure. Base conditions are at a cyclohexanone oxime solution feed rate of 1 LHSV and a nitrogen feed of 645 GHSV.

It is expected that the ZSM-5 catalyst treated with oxalic acid will show a higher yield and a lower aging in the above test than an untreated ZSM-5 catalyst.

Changes and modifications in the specifically described embodiments can be carried out without departing from the scope of the invention which is intended to be limited only by the scope of the appended claims.

What is claimed:

1. In a process for the manufacture of epsilon-caprolactam by contacting cyclohexanone oxime under conversion conditions with a catalyst composition comprising a crystalline aluminosilicate zeolite having a Constraint Index greater than 1 and an Alpha Value in the range of from about 0.1 to about 50, the improvement comprising treating said crystalline aluminosilicate zeolite with dicarboxylic acid prior to said contacting step for a sufficient time to effect at least about a 40% reduction in surface acidity with less than about 50% overall dealumination.

2. The process of claim 1 wherein said conversion conditions include a temperature in the range of about 200° to about 400° C.

3. The process of claim 1 wherein said crystalline aluminosilicate zeolite is selected from the group consisting of ZSM-5, ZSM-11, ZSM-12, and ZSM-48.

4. The process of claim 1 wherein said crystalline aluminosilicate zeolite has the structure of ZSM-5.

5. The process of claim 1 wherein said crystalline aluminosilicate zeolite is bound with a non-acidic matrix prior to said selective surface dealumination.

6. The process of claim 5 wherein said matrix is selected from the group consisting of titania, carbon, and silica.

7. The process of claim 6 wherein said matrix is silica.

8. The process of claim 1 wherein said crystalline aluminosilicate zeolite is self-bonded.

9. The process of claim 1 wherein said surface acidity is reduced by at least about 50%.

10. The process of claim 1 wherein said surface acidity is reduced by at least about 60%.

11. The process of claim 1 wherein said overall dealumination is less than about 20%.

12. The process of claim 1 wherein said overall dealumination is less than about 10%.

13. The process of claim 1 wherein said dicarboxylic acid is in solution.

14. The process of claim 13 wherein said solution of dicarboxylic acid is at a volume ratio of solution to catalyst of at least about 1:1.

15. The process of claim 1 wherein said dicarboxylic acid is an aqueous dicarboxylic acid solution.

16. The process of claim 1 wherein said dicarboxylic acid is in a concentration in the range of from about 0.01 to about 4M.

17. The process of claim 1 wherein said dicarboxylic acid is selected from the group consisting of oxalic, malonic, succinic, glutaric, adipic, maleic, phthalic, isophthalic, terephthalic, fumaric, tartaric, and mixtures thereof.

18. The process of claim 1 wherein said dicarboxylic acid is oxalic acid.

19. The process of claim 1 wherein said treating is for a time of at least about 10 minutes.

20. The process of claim 1 wherein said treating is at a temperature in the range of from about 60° F. to about 200° F.

21. In a process for the manufacture of epsilon-caprolactam by contacting cyclohexanone oxime under conversion conditions with a catalyst composition comprising a crystalline aluminosilicate zeolite having a Constraint Index greater than 1 and an Alpha Value in the range of from about 0.1 to about 50, the improvement comprising treating said crystalline aluminosilicate zeolite with oxalic acid prior to said contacting step for a sufficient time to effect at least about a 40% reduction in surface acidity with less than about 50% overall dealumination.

* * * * *

UNITED STATES PATENT AND TRADEMARK OFFICE
CERTIFICATE OF CORRECTION

PATENT NO. : 5,292,880
DATED : March 8, 1994
INVENTOR(S) : M. R. Apelian et al.

It is certified that error appears in the above-indentified patent and that said Letters Patent is hereby corrected as shown below:

On the title page, Item [54]:
In the title, add --With Reduced Surface Acidity--

Signed and Sealed this

Sixth Day of September, 1994

Attest:

BRUCE LEHMAN

Attesting Officer

Commissioner of Patents and Trademarks